US011149039B2

(12) United States Patent
Giblin et al.

(10) Patent No.: US 11,149,039 B2
(45) Date of Patent: Oct. 19, 2021

(54) PROCESS FOR PREPARING SPIRO DERIVATIVES

(71) Applicant: Biogen Inc., Cambridge, MA (US)

(72) Inventors: Gerard M. Giblin, Cambridge, MA (US); David T. MacPherson, Cambridge, MA (US); Osama Suleiman, Cambridge, MA (US); Michael Williams, Cambridge, MA (US); David R. Witty, Cambridge, MA (US); Thierry Bonnaud, Cambridge, MA (US); Richard Edwards, Cambridge (GB)

(73) Assignee: Biogen Inc., Cambridge, MA (US)

( * ) Notice: Subject to any disclaimer, the term of this patent is extended or adjusted under 35 U.S.C. 154(b) by 0 days.

(21) Appl. No.: 16/754,044

(22) PCT Filed: Oct. 10, 2018

(86) PCT No.: PCT/US2018/055227
§ 371 (c)(1),
(2) Date: Apr. 6, 2020

(87) PCT Pub. No.: WO2019/075073
PCT Pub. Date: Apr. 18, 2019

(65) Prior Publication Data
US 2020/0325144 A1    Oct. 15, 2020

Related U.S. Application Data

(60) Provisional application No. 62/570,269, filed on Oct. 10, 2017.

(51) Int. Cl.
*C07D 487/10* (2006.01)
*C07D 207/277* (2006.01)

(52) U.S. Cl.
CPC ....... *C07D 487/10* (2013.01); *C07D 207/277* (2013.01)

(58) Field of Classification Search
CPC .......................... C07D 487/10; C07D 207/277
See application file for complete search history.

(56) References Cited

U.S. PATENT DOCUMENTS

| | | | |
|---|---|---|---|
| 814,396 | A | 3/1906 | Russell |
| 5,955,606 | A | 9/1999 | Kim et al. |
| 7,655,693 | B2 | 2/2010 | Alvaro et al. |
| 7,803,833 | B2 | 9/2010 | Alvaro et al. |
| 7,855,218 | B2 | 12/2010 | Alvaro et al. |
| 8,093,268 | B2 | 1/2012 | Alvaro et al. |
| 8,143,306 | B2 | 3/2012 | Alvaro et al. |
| 8,153,623 | B2 | 4/2012 | Alvaro et al. |
| 8,153,681 | B2 | 4/2012 | Alvaro et al. |
| 8,759,542 | B2 | 6/2014 | Zajac |
| 9,309,254 | B2 | 4/2016 | Giblin et al. |
| 9,376,445 | B2 | 6/2016 | Giblin et al. |
| 9,737,536 | B2 | 8/2017 | Giblin et al. |
| 10,010,551 | B2 | 7/2018 | Giblin et al. |
| 10,485,801 | B2 | 11/2019 | Giblin et al. |
| 2008/0293753 | A1 | 11/2008 | Alvaro et al. |
| 2009/0171100 | A1 | 7/2009 | Hildbrand et al. |
| 2009/0318530 | A1 | 12/2009 | Alvaro et al. |
| 2009/0326032 | A1 | 12/2009 | Alvaro et al. |
| 2010/0105688 | A1 | 4/2010 | Alvaro et al. |
| 2010/0130583 | A1 | 5/2010 | Alvaro et al. |
| 2011/0294842 | A9 | 12/2011 | Cadieux et al. |
| 2012/0178761 | A1 | 7/2012 | Knust et al. |
| 2014/0350040 | A1 | 11/2014 | Witty et al. |
| 2015/0119404 | A1 | 4/2015 | Giblin et al. |
| 2015/0166551 | A1 | 6/2015 | Giblin et al. |
| 2015/0225400 | A1 | 8/2015 | Witty et al. |
| 2016/0184306 | A1 | 6/2016 | Giblin et al. |
| 2016/0263115 | A1 | 9/2016 | Giblin et al. |
| 2017/0226080 | A1 | 8/2017 | Heinrich et al. |
| 2020/0255438 | A1 | 8/2020 | Giblin et al. |
| 2020/0289508 | A1 | 9/2020 | Giblin et al. |
| 2020/0325144 | A1 | 10/2020 | Giblin et al. |

FOREIGN PATENT DOCUMENTS

| | | |
|---|---|---|
| CN | 101326162 A | 12/2008 |
| CN | 101522685 A | 9/2009 |
| JP | 2005536491 A | 12/2005 |
| JP | 2010516731 A | 5/2010 |
| JP | 2011516397 A | 5/2011 |
| WO | WO-2007/042239 A1 | 4/2007 |
| WO | WO-2007/042240 A1 | 4/2007 |
| WO | WO-2007/042250 A1 | 4/2007 |
| WO | WO-2008046046 A1 | 4/2008 |
| WO | WO-2008/090114 A1 | 7/2008 |
| WO | WO-2008/122546 A1 | 10/2008 |
| WO | WO-2011002708 A1 | 1/2011 |

(Continued)

OTHER PUBLICATIONS

Bagal et al., "Recent progress in sodium channel modulators for pain," Bioorganic & medicinal chemistry letters, 24(16):3690-3699 (2014).
Damasio, "Alzheimer's Disease and Related Dementias," Cecil Textbook of Medicine, 20th Edition, vol. 2, pp. 1992-1996 (1996).
Eijkelkamp et al., "Neurological Perspectives on Voltage-gated Sodium Channels," Brain: A Journal of Neurology, 135: 2585-2612 (2012).
International Preliminary Report on Patentability for International Application No. PCT/GB2013/051335 dated Nov. 24, 2014.
International Preliminary Report on Patentability for International Application No. PCT/GB2013/51336 dated Nov. 25, 2014.

(Continued)

*Primary Examiner* — Deepak R Rao
(74) *Attorney, Agent, or Firm* — David P. Halstead; Lucas P. Watkins; Foley Hoag LLP

(57) ABSTRACT

The invention relates to a novel process for preparing Spiro derivatives, in particular 7-methyl-2-[4-methyl-6-[4-(trifluoromethyl)-phenyl]pyrimidin-2-yl]-1,7-diazaspiro[4.4]nonan-6-one, and to novel intermediates for use in said process along with processes for preparing said intermediates.

19 Claims, No Drawings

(56) References Cited

FOREIGN PATENT DOCUMENTS

| WO | WO-2013/093496 A1 | 6/2013 |
|----|-------------------|--------|
| WO | WO-2013/093497 A1 | 6/2013 |
| WO | WO-2013/175205 A1 | 11/2013 |
| WO | WO-2013/179049 A1 | 12/2013 |
| WO | WO-2019/075073 A3 | 4/2019 |

OTHER PUBLICATIONS

International Search Report and Written Opinion for International Application No. PCT/GB2013/51336 dated Jul. 2, 2013.
International Search Report and Written Opinion for International Application No. PCT/US18/53520 dated Dec. 20, 2018.
International Search Report and Written Opinion for International Application No. PCT/US18/55227 dated Dec. 27, 2018.
International Search Report and Written Opinion for International Application PCT/GB2013/051335 dated Feb. 7, 2013.
Large et al., "The Efficacy of Sodium Channel Blockers to Prevent Phencyclidine-Induced Cognitive Dysfunction in the Rat: Potential for Novel Treatments for Schizophrenia," J Pharmacol Exp Ther, 338(1): 100-113 (2011).
Large et al., "The Relationship Between Sodium Channel Inhibition and Anticonvulsant Activity in a Model of Generalised Seizure in the Rat," Epilepsy Res, 85(1): 96-106 (2009).
PubChem CID: 21751157 Dec. 5, 2007.
Extended European Search Report for Application No. EP 18861356 dated Dec. 23, 2020.
Falgueyret et al., "Novel, Nonpeptidic Cyanamides as Potent and Reversible Inhibitors of Human Cathepsins K and L," J. Med. Chem. 44:94-104 (2001).
Park et al., "Supporting Information. Highly Enantioselective Phase-Transfer Catalytic α-Alkylation of α-tert-butoxylcarbonyllactams: Construction of β-Quaternary Chirla Pyrrolidine and Piperidine Systems," Adv. Synth. Catal., 353: 93 pages (2011).
Partial European Search Report for EP Application No. 18866634.1 dated Feb. 25, 2021.

PROCESS FOR PREPARING SPIRO DERIVATIVES

RELATED APPLICATIONS

This application is a National Stage of International Patent Application No. PCT/US2018/055227, filed Oct. 10, 2018, which claims the benefit of U.S. Provisional Patent Application No. 62/570,269, filed on Oct. 10, 2017, the contents of each of which are hereby incorporated by reference in their entirety.

FIELD OF THE INVENTION

The invention relates to a novel process for preparing spiro derivatives, in particular 7-methyl-2-[4-methyl-6-[4-(trifluoromethyl)-phenyl]pyrimidin-2-yl]-1,7-diazaspiro [4.4]nonan-6-one, and to novel intermediates for use in said process along with processes for preparing said intermediates.

BACKGROUND OF THE INVENTION

7-Methyl-2-[4-methyl-6-[4-(trifluoromethyl)-phenyl]pyrimidin-2-yl]-1,7-diazaspiro[4.4]nonan-6-one:

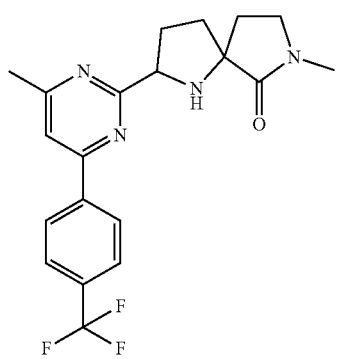

(I)

is described in WO 2013/175205 as having utility in the treatment of diseases and conditions mediated by modulation of use-dependent voltage-gated sodium channels. The synthetic preparation of 7-methyl-2-[4-methyl-6-[4-(trifluoromethyl)-phenyl]pyrimidin-2-yl]-1,7-diazaspiro[4.4] nonan-6-one is also described in WO 2013/175205.

However, there is a need for the development of alternative processes for the preparation of such spiro derivatives, which are capable of practical application to large scale manufacture.

SUMMARY OF THE INVENTION

According to a first aspect of the invention there is provided a compound which is (S)-1-methyl-2-oxo-3-(prop-2-yn-1-yl)pyrrolidine-3-carboxylic acid (D6):

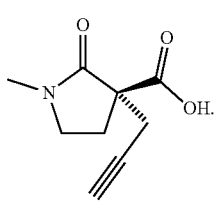

(D6)

According to a second aspect of the invention there is provided a process of preparing the compound of D6 as defined herein, from a compound which is (S)-1-methyl-2-oxo-3-(prop-2-yn-1-yl)pyrrolidine-3-carboxylic acid (S)-phenylglycinol salt (D5):

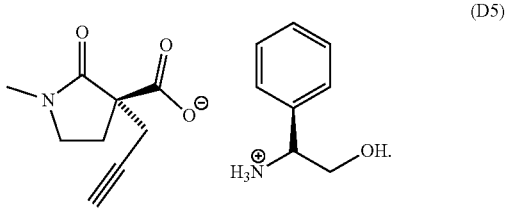

(D5)

According to a further aspect of the invention there is provided a process of preparing a compound which is 7-methyl-2-[4-methyl-6-[4-(trifluoromethyl)-phenyl]pyrimidin-2-yl]-1,7-diazaspiro[4.4]nonan-6-one, i.e. a compound of formula (I):

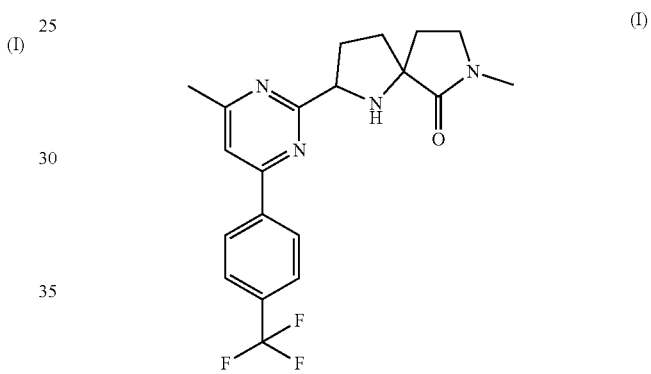

(I)

which comprises:
steps (i) to (v) as defined herein or steps (a) to (c) followed by steps (iii) to (v) as defined herein; followed by:
(vi) preparing a compound of D9:

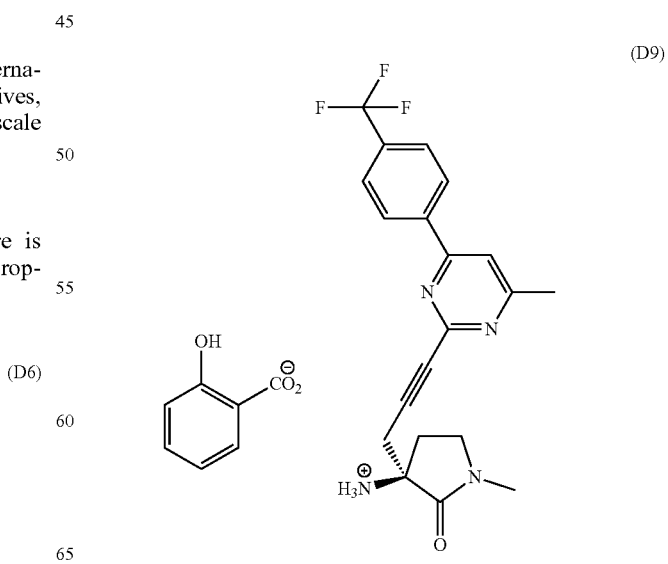

(D9)

from a compound of D7:

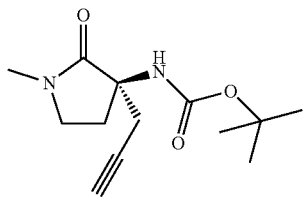
(D7)

and a compound of D8:

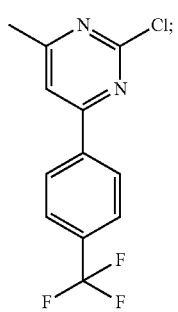
(D8)

followed by (vii) preparing a compound of D10:

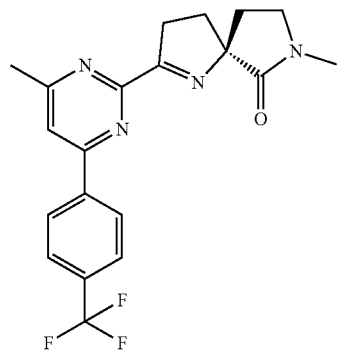
(D10)

from a compound of D9; followed by (viii) preparing a compound of formula (I)

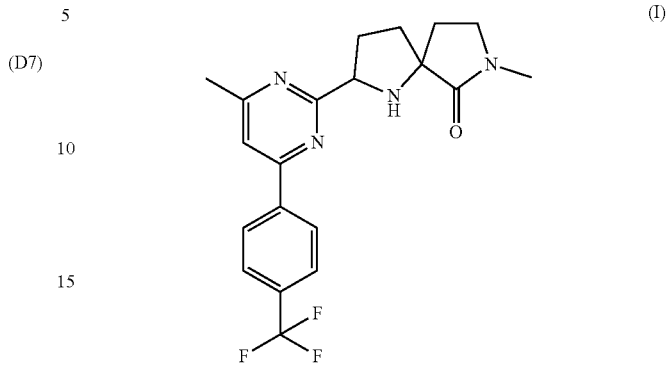
(I)

from a compound of D10.

DETAILED DESCRIPTION OF THE INVENTION

According to a first aspect of the invention there is provided a compound which is (S)-1-methyl-2-oxo-3-(prop-2-yn-1-yl)pyrrolidine-3-carboxylic acid (D6):

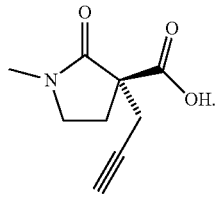
(D6)

Detailed methodology of the preparation of the compound of D6 is described herein as Description 6.

According to a second aspect of the invention there is provided a process of preparing the compound of D6 as defined herein, from a compound which is (S)-1-methyl-2-oxo-3-(prop-2-yn-1-yl)pyrrolidine-3-carboxylic acid (S)-phenylglycinol salt (D5):

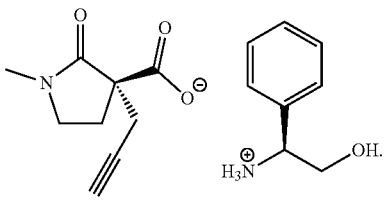
(D5)

In one embodiment of the second aspect of the invention, the carboxylic acid compound of D5 may be protonated by treatment in a suitable solvent (such as MeOH:water, (80:20)) with an acidic ion exchange resin.

The novel intermediate and resultant process of the present invention provides a number of advantages. For example, in comparison with the previously described synthetic route for preparing the compound of formula (I) the process of the present invention contains fewer stages, uses cheaper starting materials and avoids the need for burdensome chromatography.

The novel intermediate of the present invention finds particular utility as a precursor of tert-butyl N-[(3S)-1-methyl-2-oxo-3-prop-2-ynyl-pyrrolidin-3-yl]carbamate (described as Description D4 in WO 2013/175205) which itself is a key intermediate in the preparation of a compound of formula (I). Thus, according to a further aspect of the invention there is provided a process of preparing a compound which is (S) tert-butyl (1-methyl-2-oxo-3-(prop-2-yn-1-yl)pyrrolidin-3-yl)carbamate (D7):

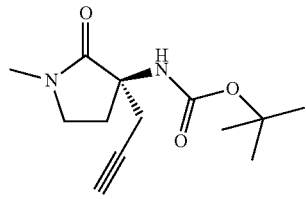

(D7)

which comprises:
(i) preparing a compound of D1:

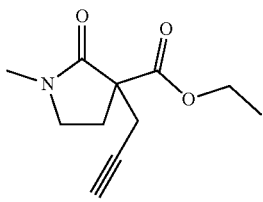

(D1)

from 1-methylpyrrolidin-2-one; followed by
(ii) preparing a compound of D4:

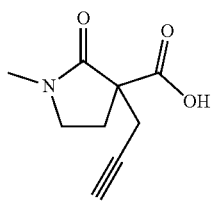

(D4)

from a compound of D1; followed by
(iii) preparing a compound of D5:

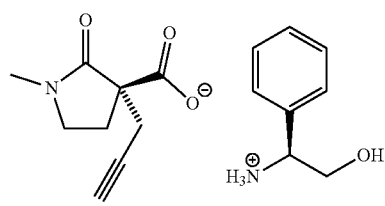

(D5)

from a compound of D4; followed by
(iv) preparing a compound of D6:

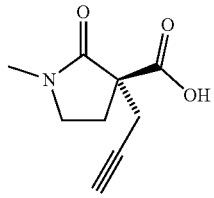

(D6)

from a compound of D5; and followed by
(v) preparing a compound of D7:

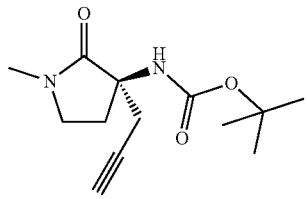

(D7)

from a compound of D6.

In one embodiment, step (i) typically comprises cooling a solution of a suitable base (such as lithium diisopropylamide, LDA, available commercially or prepared in situ from diisopropylamine and n-butyl lithium) in a suitable solvent (such as THF) to a suitable temperature (such as −10° C.) prior to addition of 1-methylpyrrolidin-2-one to the resulting solution while stirring at a suitable temperature (such as 0° C.) for a suitable duration (such as 15 minutes) followed by addition of diethyl carbonate and stirring at a suitable temperature (such as ambient) for a suitable duration (such as 4 hours) followed by cooling to a suitable temperature (such as −5° C.) followed by addition of 3-bromoprop-1-yne followed by stirring at a suitable temperature (such as ambient) for a suitable time (such as overnight). Full experimental details of step (i) are provided herein in Description 1.

In one embodiment, step (ii) typically comprises addition of a suitable reagent (such as sodium hydroxide) to a solution of the compound of D1 in a suitable solvent (such as THF). Full experimental details of step (ii) are provided herein in Description 4 (Method A).

In one embodiment, step (iii) typically comprises dissolving the compound of D4 in a suitable solvent (such as IPA) at a suitable temperature (such as 50° C.) followed by addition of a suitable reagent (such as S-(+)-2-phenylglycinol) dissolved in a suitable solvent (such as water) followed by cooling and seeding at a suitable temperature (such as 41° C.) followed by further cooling and isolation of the resulting solid. Full experimental details of step (iii) are provided herein in Description 5.

In one embodiment, step (iv) typically comprises protonating the carboxylic acid compound of D5 by treatment in a suitable solvent (such as MeOH:water, (80:20)) with an acidic ion exchange resin. Full experimental details of step (iv) are provided herein in Description 6.

In one embodiment, step (v) typically comprises adding a suitable reagent (such as diphenylphosphorylazide) to a suspension of a compound of D6 in a suitable solvent (such as toluene) and a suitable base (such as triethylamine) followed by stirring at a suitable temperature (such as room temperature) for a suitable duration (such as 1 hour) followed by heating to a suitable temperature (such as 80° C.) for a suitable time (such as 2 hours) followed by cooling and addition of suitable reagents (such as DMAP and tert-butanol) followed by reheating to a suitable temperature (such as 80° C.) for a suitable time (such as overnight). Full experimental details of step (v) are provided herein in Description 7. The compound of D7 corresponds to the compound of D4 in WO 2013/175205.

The present invention provides two differing routes to prepare the compound of D4. In the previous aspect of the invention the compound of D4 is prepared directly from the compound of D1. In the aspect of the invention which follows, the compound of D4 is prepared sequentially from D2 and then D3.

Thus, according to a further aspect of the invention there is provided a process of preparing a compound which is (S) tert-Butyl (1-methyl-2-oxo-3-(prop-2-yn-1-yl)pyrrolidin-3-yl)carbamate (D7):

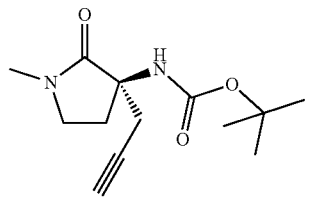

(D7)

which comprises:
(a) preparing a compound of D2:

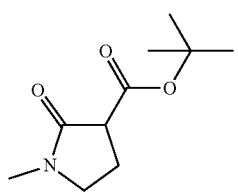

(D2)

from 1-methylpyrrolidin-2-one; followed by
(b) preparing a compound of D3:

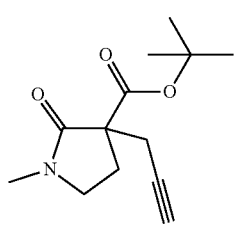

(D3)

from a compound of D2; followed by
(c) preparing a compound of D4:

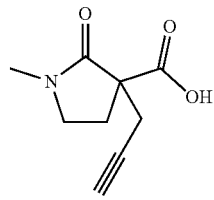

(D4)

from a compound of D3; followed by
(iii) preparing a compound of D5:

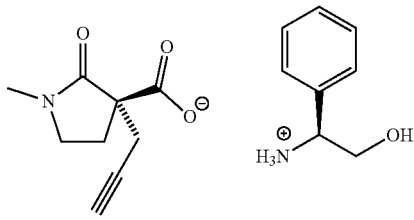

(D5)

from a compound of D4; followed by
(iv) preparing a compound of D6:

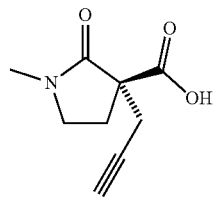

(D6)

from a compound of D5; and followed by
(v) preparing a compound of D7:

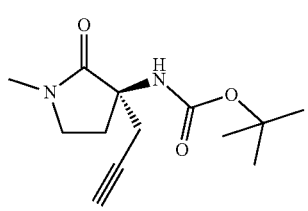

(D7)

from a compound of D6.

In one embodiment, step (a) typically comprises cooling a solution of a suitable base (such as lithium diisopropyl-amide, LDA, available commercially or prepared in situ) in a suitable solvent (such as THF) to a suitable temperature (such as 0° C.) followed by the dropwise addition of 1-methylpyrrolidin-2-one followed by stirring for a suitable time (such as 30 minutes) followed by addition of a solution of a suitable reagent (such as di-tert-butyl dicarbonate) in THF followed by stirring at a suitable temperature (such as ambient) for a suitable time (such as 4 hours). Full experimental details of step (a) are provided herein in Description 2.

In one embodiment, step (b) typically comprises adding suitable reagents (such as tetrabutylammonium bromide and propargyl bromide) to a solution of a compound of D2 in a suitable solvent (such as toluene) followed by addition of a suitable reagent (such as ground potassium hydroxide) and then stirring the mixture at a suitable temperature (such as room temperature). Full experimental details of step (b) are provided herein in Description 3.

In one embodiment, step (c) typically comprises adding a suitable reagent (such as TFA) to a solution of a compound of D3 in a suitable solvent (such as dichloromethane) followed by stirring the solution at a suitable temperature (such as room temperature) for a suitable duration (such as overnight). Full experimental details of step (c) are provided herein in Description 4 (Method B).

It will be appreciated that steps (iii), (iv) and (v) may be conducted in the same manner as those described in the previous aspect of the invention.

The compound of D6 and other intermediates described herein represent valuable intermediates in the preparation of spiro derivatives, such as the compound of formula (I).

Examples of spiro compounds which may be prepared using the compound of D6 and other intermediates described herein include those described in WO 2013/175206 and in particular those described in WO 2013/175205.

Thus, according to a further aspect of the invention there is provided a process of preparing a compound which is 7-methyl-2-[4-methyl-6-[4-(trifluoromethyl)-phenyl]pyrimidin-2-yl]-1,7-diazaspiro[4.4]nonan-6-one, i.e. a compound of formula (I):

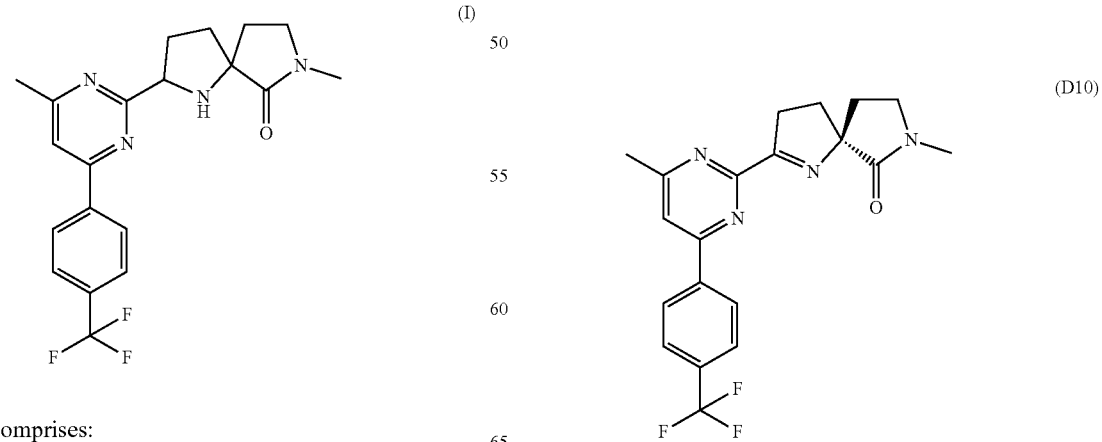

which comprises:
steps (i) to (v) as defined herein; or steps (a) to (c) followed by steps (iii) to (v) as defined herein; followed by:

(vi) preparing a compound of D9:

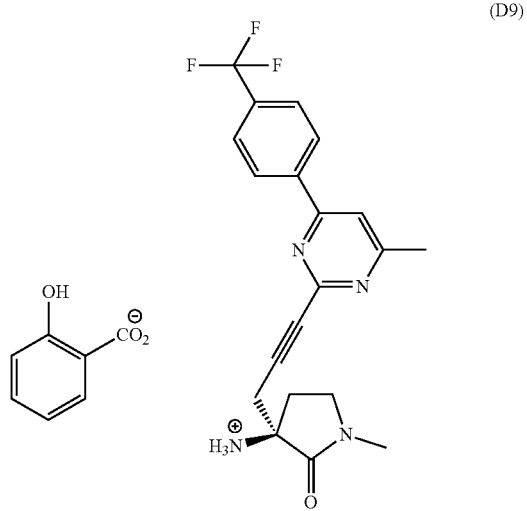

from a compound of D7 and a compound of D8:

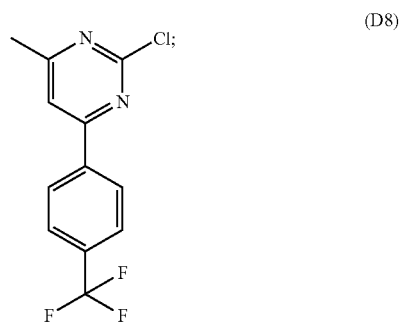 [SMILES: Cc1cc(-c2ccc(C(F)(F)F)cc2)nc(Cl)n1]

followed by
(vii) preparing a compound of D10:

(D10)

from a compound of D9; followed by
(viii) preparing a compound of formula (I):

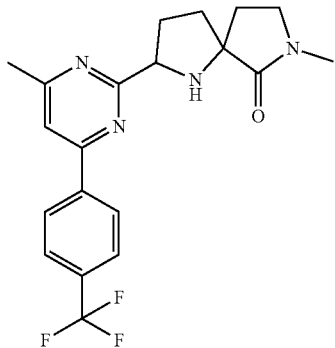

from a compound of D10.

In one embodiment, the compound of formula (I) is a compound of formula (Ia):

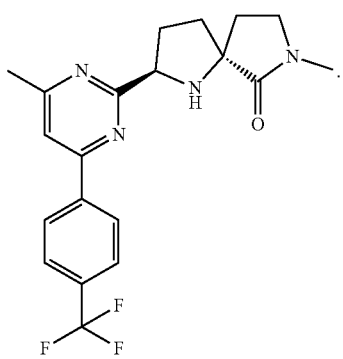

In a further embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one hydrochloride. This compound corresponds to Example 1 in WO 2013/175205.

In a further embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one sulfuric acid salt. The preparation of the compound of this embodiment is described herein as Example 1 (E1) and this compound corresponds to Example 2 in WO 2013/175205.

In a further embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one sulfuric acid salt hydrate. This compound corresponds to Example 3 in WO 2013/175205.

In a further embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one citric acid (citrate) salt.

In a further embodiment, the compound of formula (I) is (2R,5S)-7-methyl-2-[4-methyl-6-[4-(trifluoromethyl)-phenyl]pyrimidin-2-yl]-1,7-diazaspiro[4.4]nonan-6-one methanesulfonic acid (mesylate) salt.

In one embodiment, step (vi) typically comprises combining a compound of D7 and a compound of D8 in the presence of a suitable solvent (such as isopropyl acetate) and a suitable base (such as triethylamine) and a suitable catalyst (such as PdCl$_2$(PPh$_3$)$_2$ and CuI) followed by heating at a suitable temperature (such as 80° C.) for a suitable time (such as 18.5 hours), followed by work up and then reaction of the isolated product in a suitable solvent (such as dichloromethane) with a suitable reagent (such as methanesulfonic acid) for a suitable time (such as 1.5 hours) at a suitable temperature (such as ambient), followed by isolation and free basing of the amine with a suitable base (such as potassium phosphate) followed by reaction of the amine in a suitable solvent (such as acetonitrile) with a suitable acid (such as salicylic acid) at a suitable temperature (such as 40-45° C.) to form a solid product which is isolated after cooling to a suitable temperature (such as 0±5° C.) Full experimental details of step (vi) are provided herein in Description 9. The compound of D9 is a salted form of D8 described in WO 2013/175205.

In one embodiment, step (vii) typically comprises freebasing the compound of D9 in a suitable solvent (such as methylene chloride) with a suitable base (such as a 20% aqueous solution of potassium phosphate)), followed by exchange of the solvent to a more suitable solvent (such as acetonitrile) followed by treatment with a suitable reagent (such as silver trifluoromethanesulfonate) and heating to a suitable temperature (such as 74° C.) for a suitable time (such as 46 hours). Full experimental details of step (vii) are provided herein in Description 10. The compound of D10 herein corresponds to the compound of D9 described in WO 2013/175205.

In one embodiment, step (viii) typically comprises treating the compound of D10 in a suitable solvent (such as methylene chloride) at a suitable temperature (such as −23° C.) with a suitable reagent (such as borane tert-butylamine complex) in a suitable solvent (such as dichloromethane) followed by stirring at a suitable temperature (such as −13° C.) for a suitable time (such as 1.5 hours) followed by quenching the reaction with a suitable reagent (such as 5M HCl) at a suitable temperature (such as 20° C.) followed by work up with a suitable base (such as potassium phosphate solution) and treatment of the product in a suitable solvent (such as acetonitrile) with a suitable reagent (such as 7.5M sulphuric acid) followed by recrystallisation of the resulting solid from a suitable solvent (such as acetone/water). Full experimental details of step (viii) are provided herein in Example 1. The compound of E1 herein corresponds to Example 2 in WO 2013/175205.

According to a further aspect of the invention there is provided a process of preparing a compound which is D1:

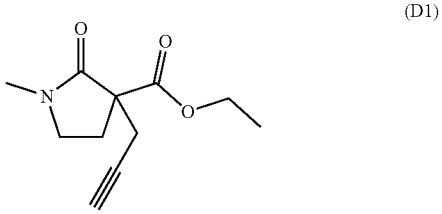

from 1-methylpyrrolidin-2-one.

According to a further aspect of the invention there is provided a process of preparing a compound of D2:

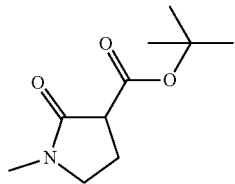
(D2)

from 1-methylpyrrolidin-2-one.

According to a further aspect of the invention there is provided a process of preparing a compound of D3:

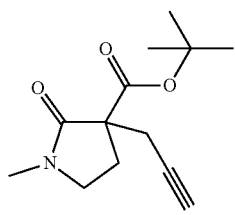
(D3)

from a compound of D2.

According to a further aspect of the invention there is provided a process of preparing a compound of D4:

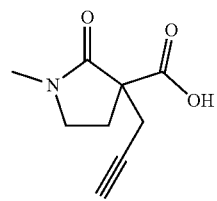
(D4)

from a compound of D3.

According to a further aspect of the invention there is provided a process of preparing a compound of D4:

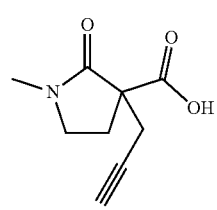
(D4)

from a compound of D1.

According to a further aspect of the invention there is provided a process of preparing a compound of D5:

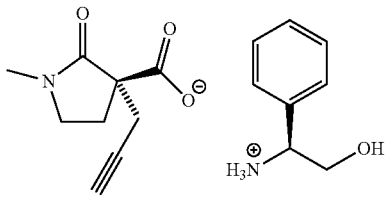
(D5)

from a compound of D4.

According to a further aspect of the invention there is provided a process of preparing a compound of D7:

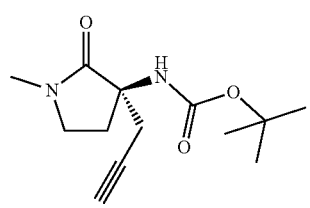
(D7)

from a compound of D6.

According to a further aspect of the invention there is provided a process of preparing a compound of D9:

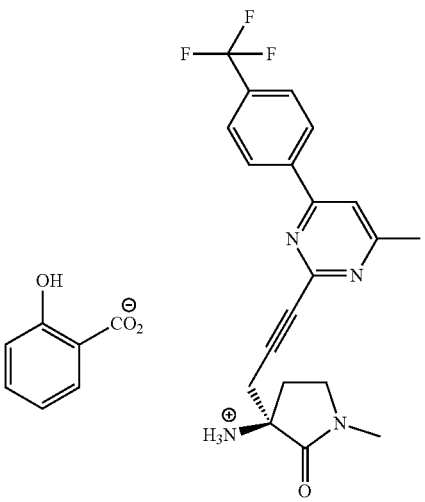
(D9)

from a compound of D7 and a compound of D8:

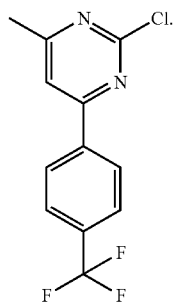

According to a further aspect of the invention there is provided a process of preparing a compound of D10:

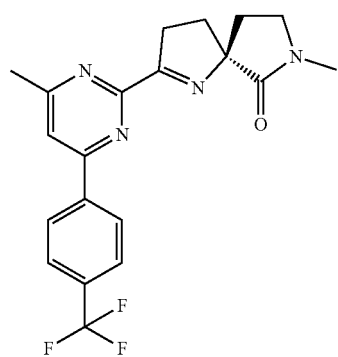

from a compound of D9.

According to a further aspect of the invention there is provided a process of preparing a compound of formula (I):

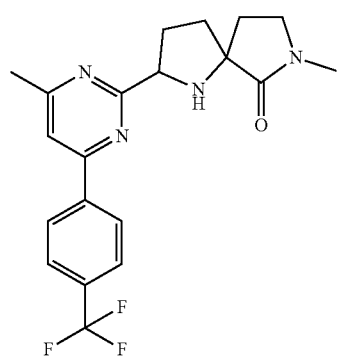

from a compound of D10.

EXAMPLES

The invention is illustrated by the Examples described below. The following examples are included merely for purposes of illustration of certain aspects and embodiments of the present invention, and are not intended to limit the invention.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Experimental

General

Proton Magnetic Resonance (NMR) spectra are typically recorded on a Bruker instruments at 300, 400 or 500 MHz. Chemical shifts are reported in ppm (δ) using the residual solvent line as internal standard. Splitting patterns are designated as s, singlet; d, doublet; t, triplet; q, quartet; m, multiplet; br, broad. The NMR spectra were recorded at a temperature ranging from 25 to 90° C.

Chiral purity analysis was performed on an Agilent HP1100 series system equipped with a diode array using the following methods:

Method A
Column: Chiral Pak IA, 4.6×250 mm, 5 µm
Mobile phase: 10% ethanol with 0.1% TFA in n-heptane, 1 ml/min
Temperature: 25° C.
Detection wavelength: 215 nm
Method B
Column: Chiral Pak IA, 4.6×250 mm, 5 µm
Mobile phase: 30% ethanol with 0.1% diethylamine in n-heptane, 1 ml/min
Temperature: 25° C.
Detection wavelength: 215 nm Description 1

Ethyl 1-methyl-2-oxo-3-(prop-2-yn-1-yl)pyrrolidine-3-carboxylate (D1)

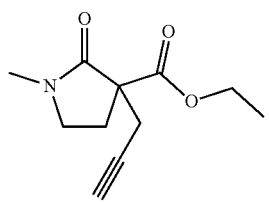

To a solution of diisopropylamine (104.9 mL, 748.1 mmol) in THF (345 mL) cooled to −10° C. (salt/ice bath) stirred using an overhead stirrer was added n-butyllithium (2.5M solution in hexanes, 299.2 mL, 748.1 mmol) dropwise over 40 mins. The resulting solution was stirred at 0° C. over 15 mins then 1-methylpyrrolidin-2-one (36 mL, 374.1 mmol) was added dropwise over 20 mins. The resulting solution was stirred at 0° C. over 15 mins then diethyl carbonate (45.3 mL, 374.1 mmol) was added dropwise over 20 mins resulting in a suspension. The reaction mixture was allowed to warm to room temperature and stirred over 4 hrs, giving a thick precipitate. The mixture was cooled to −5° C. and 3-bromoprop-1-yne (80% w/w in toluene, 52.1 mL, 374.1 mmol) was added dropwise. The mixture was allowed to warm slowly to room temperature with stirring overnight to give a solution. The solution was cooled to 0° C. and sat. ammonium chloride (350 mL) was added dropwise followed by EtOAc (500 mL) and the mixture stirred for 10 minutes. The mixture was filtered over Celite and the filter cake was washed with EtOAc (2×250 mL). The filtrate phases were separated and the aq. phase was extracted with EtOAc (2×500 ml) and the combined organics were dried over magnesium sulphate, filtered and evaporated to an oily solid. The solid was suspended in diethyl ether (1 L) and the mixture stirred for 5 minutes then filtered, the solids washed with diethyl ether (2×50 mL) and the combined filtrates evaporated to an orange oil. The material was dissolved in MTBE (500 mL) and charcoal (2.5 g) was added. The mixture was stirred and heated to reflux then allowed to cool back to room temperature, filtered over celite, washed through with further MTBE and the filtrate evaporated to afford ethyl 1-methyl-2-oxo-3-prop-2-ynyl-pyrrolidine-3-carboxylate (D1) as an orange oil (49.74 g, 64%). 300 MHz NMR $\delta_H$ (CDCl$_3$) 1.26 (3H, t), 1.95 (1H, t), 2.26-2.36 (1H, m), 2.47-2.55 (1H, m), 2.73-2.87 (2H, m), 2.90 (3H, s), 3.33-3.40 (1H, m), 3.46-3.55 (1H, m), 4.20 (2H, q).

Description 2

Tert-Butyl 1-methyl-2-oxo-pyrrolidine-3-carboxylate (D2)

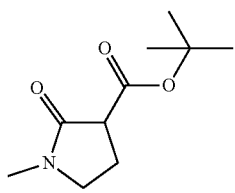

A solution of diisopropylamine (14.1 mL, 101 mmol) in THF (100 mL) was cooled to −78° C. and n-butyllithium (42.3 mL of a 2.5 M solution in hexane, 106 mmol) was added dropwise over 10 minutes and the solution was then stirred at −78° C. for 30 minutes. The reaction mixture was warmed to 0° C. and 1-methylpyrrolidin-2-one (4.85 mL, 50.4 mmol) was added dropwise. The solution was stirred for a further 30 minutes. A solution of di-tert-butyl dicarbonate (11.0 g, 50.4 mmol) in THF (20 mL) was added dropwise and then the reaction mixture was brought to room temperature and stirred.

After 4 hours, the mixture was cooled in an ice-bath and aqueous saturated ammonium chloride solution (20 mL) was added dropwise. The volatiles were removed under reduced pressure and the resultant solution was diluted with a further portion of aqueous saturated ammonium chloride solution (50 mL). The aqueous was extracted with diethyl ether (2×100 mL) and the combined organics were dried (Na$_2$SO$_4$) and concentrated to give a pale yellow oil. The oil was purified using column chromatography (SiO$_2$) eluting over a 0-100% gradient of ethyl acetate in iso-hexane. The title compound (D2) was isolated as an off-white oil (7.70 g, 38.6 mmol, 77%).

300 MHz NMR (CDCl$_3$) $\delta_H$: 1.48 (s, 9H), 2.15-2.39 (m, 2H), 2.86 (s, 3H), 3.26-3.35 (m, 2H), 3.43-3.51 (m, 1H).

Description 3

Tert-Butyl 1-methyl-2-oxo-3-prop-2-ynyl-pyrrolidine-3-carboxylate (D3)

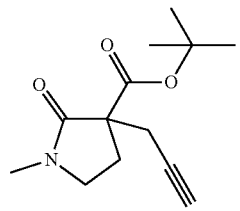 [SMILES: C#CCC1(C(=O)OC(C)(C)C)CCN(C)C1=O]

To a solution of tert-butyl 1-methyl-2-oxo-pyrrolidine-3-carboxylate (D2) (200 mg, 1.00 mmol) in toluene (5 mL) was added tetrabutylammonium bromide (32 mg, 0.10 mmol) and propargyl bromide (0.56 mL, 5.02 mmol). Ground potassium hydroxide (282 mg, 5.02 mmol) was added and the mixture was stirred at room temperature. After 45 minutes the reaction mixture was diluted with ethyl acetate (20 mL) and washed with brine (15 mL). The aqueous was washed with a further portion of ethyl acetate (10 mL) and the combined organics were dried (Na$_2$SO$_4$) and concentrated under reduced pressure to give a brown oil.

The oil was purified using column chromatography (SiO$_2$) eluting over a 0-100% ethyl acetate in iso-hexane gradient to give the title compound (D3) as an off-white solid (226 mg, 0.95 mmol, 95%).

LCMS (m/z): 238.1 (MH)$^+$

300 MHz NMR (CDCl$_3$) $\delta_H$: 1.45 (s, 9H), 1.95 (t, 1H), 2.25-2.48 (m, 2H), 2.76 (2×dd, 2H), 2.90 (s, 3H), 3.31-3.39 (m, 1H), 3.44-3.50 (m, 1H).

Description 4

1-Methyl-2-oxo-3-(prop-2-yn-1-yl)pyrrolidine-3-carboxylic acid (D4)

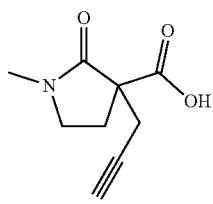

Method A

To a solution of ethyl 1-methyl-2-oxo-3-prop-2-ynyl-pyrrolidine-3-carboxylate (D1) (49.74 g, 237.72 mmol) in THF (125 mL) was added 30% aq. Sodium hydroxide (63.39 mL, 475.43 mmol) and the mixture was stirred vigorously at room temperature overnight giving a precipitate. The reaction mixture was acidified with conc. HCl to pH2 and extracted into EtOAc (3×100 ml). The combined extracts were dried over magnesium sulphate, filtered and evaporated to a dark brown oil which solidified on standing. The solids were dissolved in refluxing acetone (40 ml) and allowed to cool to room temperature, MTBE (20 mL) was added. The solids were filtered off and washed with 1:1 acetone:MTBE (2×10 ml) then MTBE (10 mL) and dried to afford 1-methyl-2-oxo-3-prop-2-ynyl-pyrrolidine-3-carboxylic acid (D4) as a pale yellow solid (24.89 g, 58%)

300 MHz NMR $\delta_H$ (CDCl$_3$) 2.02 (1H, t), 2.31-2.40 (1H, m), 2.55-2.64 (1H, m), 2.73-2.86 (2H, m), 2.94 (3H, s), 3.47 (2H, t).

Method B

To a solution of tert-butyl 1-methyl-2-oxo-3-prop-2-ynyl-pyrrolidine-3-carboxylate (D3) (4.00 g, 16.9 mmol) in dichloromethane (50 mL) was added TFA (12.9 mL, 169 mmol) and the solution was stirred at room temperature overnight. The solution was diluted with toluene (100 mL) and concentrated under reduced pressure. The resultant residue was azeotroped with toluene (2×50 mL) to give the acid as a brown solid (ca. 4 g).

The solid was dissolved in acetone (10 mL, with heating) and iso-hexane (5 mL) was added. Sonication caused a precipitate to form which was filtered and washed with a 1:1 acetone:iso-hexane to give the title compound as an off-white solid (1.37 g). The mother liquor was concentrated and the process was repeated to give a second batch of acid as a slightly darker solid (0.81 g). Overall yield of combined batches (D4)=2.18 g, 12.0 mmol, 71% yield.

Description 5

(S)-1-Methyl-2-oxo-3-(prop-2-yn-1-yl)pyrrolidine-3-carboxylic acid (S)-phenylglycinol salt (D5)

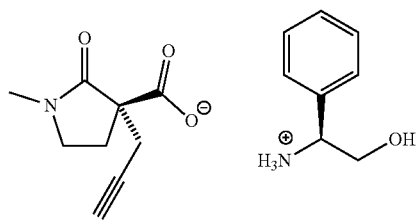

Racemic 1-methyl-2-oxo-3-(prop-2-yn-1-yl)pyrrolidine-3-carboxylic acid (D4) (8.25 g) was dissolved in IPA (61 ml) at 50° C. To the solution was added 1 mol eq. of S-(+)-2-phenylglycinol (6.245 g) dissolved in water (4.6 ml). The solution was cooled to 41° C. at 0.25° C./min, then seeded with a few crystals of pure (S)-1-methyl-2-oxo-3-(prop-2-yn-1-yl)pyrrolidine-3-carboxylic acid (S)-phenylglycinol salt and cooled to 5° C. at 0.25° C./min and the resulting suspension was left to stir at 5° C. for 12 hr, then filtered under vacuum for 10 mins. The cake was resuspended in ice-cold TBME (40 ml) and dried under vacuum at RT to yield 6.6 g, 91% of title compound (D5).

Purity by chiral HPLC (Method A)=98.9% S to 1.1% R
400 MHz NMR (D$_2$O) $\delta_H$: 2.32 (3H, m), 2.60-2.73 (2H, m), 2.88 (3H, s), 3.45-3.56 (2H, m), 3.91-4.91 (2H, m), 4.48 (1H, dd, J=5.0, 7.7 Hz), 7.44-7.52 (5H, m) ppm Exchangeables not reported.

Recrystallisation of S-Salt to Increase Chiral Purity

Samples of lower chiral purity can be recrystallized to increase chiral purity e.g.

A sample of (S) salt (4.4 g chiral purity of S-salt of 90%) was dissolved in 7 vol. of IPA/water (95:5 v/v) whilst stirring at 54° C. then cooled at 0.25° C./min to 5° C., and held overnight at 5° C. The solid was filtered and dried in a vacuum oven at RT for 6 hrs.

The yield of solid was 82% (3.6 g), with a chiral purity (after extraction of free acid in DCM/HCl aq.) of 99.5% S Description 6

(S)-1-Methyl-2-oxo-3-(prop-2-yn-1-yl)pyrrolidine-3-carboxylic acid (D6)

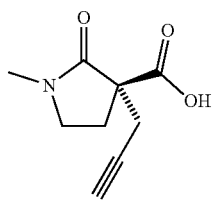

(S)-1-Methyl-2-oxo-3-(prop-2-yn-1-yl)pyrrolidine-3-carboxylic acid (S)-phenylglycinol salt (440 mg, 97.0% S; which may be prepared as described in D5) was dissolved MeOH:water (80:20) (1.5 ml). Dowex (50WX4) resin (5 ml) was added into a 10 ml syringe with frit filter. The resin was washed with 2 column volumes of water, then 4 column volumes of MeOH:water (80:20). The sample was added to the resin and eluted with 2 column volumes of MeOH:water (80:20). After evaporation of the first eluted fraction 206 mg (82% yield) of S-chiral free acid (D6) was obtained.

Chiral HPLC (Method A) 97.7% S

Description 7

(S) tert-Butyl (1-methyl-2-oxo-3-(prop-2-yn-1-yl)pyrrolidin-3-yl)carbamate (D7)

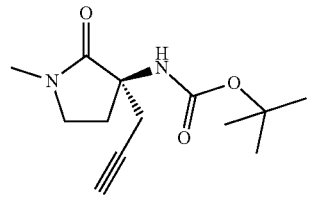 [SMILES: C#CC[C@]1(NC(=O)OC(C)(C)C)CCN(C)C1=O]

To a suspension of (S)-1-methyl-2-oxo-3-prop-2-ynyl-pyrrolidine-3-carboxylic acid (which may be prepared as described in Description 6) (606 mg, 3.34 mmol) in Toluene (8 mL) was added diphenylphosphorylazide (0.74 mL, 3.41 mmol) and triethylamine (0.47 mL, 3.34 mmol) and the solution was stirred at room temperature for 1 hour. The reaction was then heated to 80° C. for 2 hrs, slow evolution of gas was evident during heating. The mixture was cooled and 4-(dimethylamino)pyridine (179.79 mg, 1.47 mmol) and tert-butanol (1.76 mL, 16.72 mmol) were added and the mixture was stirred at 80° C. overnight.

The reaction mixture was cooled and diluted with DCM (~20 mL), washed with 1M HCl (2×20 mL) then sat aq sodium bicarbonate (2×20 mL) then dried over magnesium sulphate, filtered and evaporated to a pale yellow solid, 612 mg (D8)

300 MHz NMR (CDCl$_3$) $\delta_H$: 1.40 (9H, s), 2.0 (1H, t), 2.40-2.60 (3H, m), 2.80 (1H, m), 2.92 (3H, s), 3.40 (2H, m), 5.25 (1H, br, s) ppm.

Chiral HPLC (Method B) 95.4% S

Description 8

2-Chloro-4-methyl-6-(4-(trifluoromethyl)phenyl)pyrimidine (D8)

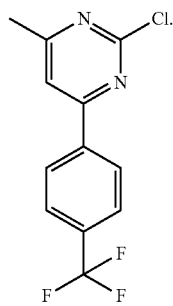 [SMILES: Cc1cc(-c2ccc(C(F)(F)F)cc2)nc(Cl)n1]

A 100 L reactor flushed with Ar, was charged with H₂O (7597 g) and iPrOH (12707 g) and the solution was degassed for 1 hour by sparging Ar. (4-(trifluoromethyl)phenyl)boronic acid (1800 g) was charged and the mixture stirred for 30 minutes then 2,4-dichloro-6-methylpyrimidine (1544 g was added and again the mixture was stirred for 30 minutes. K₂CO₃ (2621 g) and PdCl₂(PPh₃)₂ (35 g) were sequentially added. The solution was stirred and the solids slowly dissolved. The solution was heated to 60° C. and was stirred at 60° C. for 16 hrs. The solution was cooled to 5° C. and solid began to precipitate. Water (40.26 kg) was added dropwise whilst maintaining the temperature between, 5-10° C. (Note: It took 3.5 hours to complete the addition of water and a large amount of solid crash out). The mixture was stirred for 1 h 45 min at 5° C. The solid was collected by filtration under reduced pressure using a Buchner funnel (20' in diameter). The flask was rinsed with water (6316 g) and this was transferred to wash the cake. The filter cake was washed with more water (3158 g) and was suction dried on the filter for 5 hours until no liquid was collected. The solid filter cake was returned to the reactor, n-heptane (3218 g) was charged and distilled. Further azeotroping with heptane (2×3218 g, 1×1050 g and 1×720 g) was carried out and then n-heptane (3218 g) was added to the reactor and the and the temperature was adjusted to 60-70° C., until all solid dissolved. A further portion of n-heptane (429 g) was added to the reactor and mixture was filtered hot under reduce pressure using a Buchner funnel. The filtrate was transferred to a new flask and the internal temperature was adjusted to 20° C. (during cooling, a solid came out of solution). The mixture was stirred for 4 hours on ice bath. The resulting solid was collected by filtration under reduced pressure using a Buchner funnel. The flask was rinsed with n-heptane (3158 g) and this was used to wash the filter cake using agitation and the cake was and sucked dry. Washing of the filter cake as above was repeated with n-heptane (3×3158 g). The filter cake was transferred to a new flask and n-heptane (3.2 kg) was added and the mixture was heated to 60-70° C., until all solid dissolved. After stirring for 1 hour, the temperature was reduced to 20° C. and then to 0° C. slowly and the mixture was stirred for 2 hours. The solid was collected by filtration under reduced pressure using a Buchner funnel and the filter cake was washed with n-heptane (3.2 kg). Drying of the product under vacuum (35° C./−0.9 MPa) under a stream of nitrogen to constant weight to constant weight gave product as a light yellow solid (1331.1 g). Yields of 52-60% were generally obtained for this step.

Description 9

(S)-3-Amino-1-methyl-3-(3-(4-methyl-6-(4-(trifluoromethyl)phenyl)pyrimidin-2-yl)prop-2-yn-1-yl)pyrrolidin-2-one 2-hydroxybenzoate (D9)

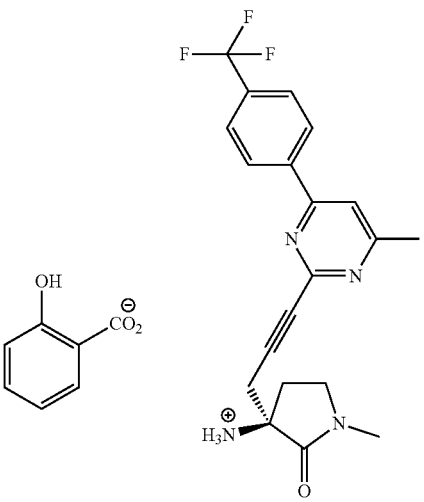

To a 100-L jacketed reactor equipped with overhead stirring, temperature probe, nitrogen inlet, and a condenser was charged 2-chloro-4-methyl-6-(4-(trifluoromethyl)phenyl)pyrimidine (4750 g, 17.4 mol, 1.00 eq; which may be prepared as described in D8), (S)-tert-butyl (1-methyl-2-oxo-3-(prop-2-yn-1-yl)pyrrolidin-3-yl)carbamate (4400 g, 17.4 mol, 1.00 eq; which may be prepared as described in D7), isopropyl acetate (60 kg, 14.5 vol), and triethylamine (5294 g, 52.3 mol, 3.00 eq). The resulting solution was degassed by bubbling nitrogen into the solution for 40 minutes. To the degassed solution was charged dichloro{bis[2-(diphenylphosphino)phenyl]ether}palladium(II) (125 g, 0.17 mol, 0.01 eq) and copper(I) iodide (67 g, 0.35 mol, 0.02 eq). The resulting bright yellow slurry was degassed for an additional 15 minutes, during which the mixture turned dark brown. The reaction mixture was heated to 80° C. and was stirred at 80±5° C. for 18.5 hours. The reaction mixture was cooled to 15° C. and the triethylamine salts were filtered onto an 18" filter funnel (5 μm nylon filter cloth used). The reactor and salts were rinsed with isopropyl acetate (8.3 kg, 2.0 vol). The jacketed reactor was cleaned with purified water, ammonium hydroxide solution, purified water, acetonitrile, and isopropyl acetate to remove any excess palladium and copper from the reactor.

The product-containing filtrate and rinse were concentrated to near-dryness by rotary evaporation on two rotavaps maintaining full vacuum and a bath temperature ≤40° C. The oil on the rotavaps was chased with methylene chloride (2×11.4 kg, 1.8 vol each) and methylene chloride (11.3 kg, 1.8 vol) was charged to the rotavaps to dilute the batch. Samples were taken from each rotavap and were analyzed separately by 1H NMR which showed an average of 4 mol % isopropyl acetate remaining (with respect to methylene chloride). The batch was charged to the cleaned jacketed reactor and the rotavap flasks were rinsed with methylene chloride (11.3 kg, 1.8 vol), which was transferred into the reactor. Additional methylene chloride (56 kg, 8.9 vol) was charged to the reactor to dilute the batch. To the product solution was charged methanesulfonic acid (6.8 kg, 70.9 mol, 4.07 eq) over 45 minutes. Once the addition was completed, agitation of the batch was increased, which allowed for minor off-gassing to occur. The reaction solution was stirred at 20±5° C. for 1.5 hours. Approximately half of the batch was drained to carboys as a second portion of the batch.

To the remainder of the batch in the jacketed reactor was charged purified water (30 kg, 12.6 vol), the biphasic reaction mixture was stirred for 35 minutes and the bottom organic layer was removed. To the top aqueous layer was charged methylene chloride (15 kg, 4.8 vol), the biphasic reaction mixture was stirred for 5 minutes and the bottom organic layer was removed. To the top aqueous layer was charged a 50% potassium phosphate solution (27.7 kg) to reach a pH of 11.6, followed by methylene chloride (22 kg, 7.0 vol). The biphasic mixture was stirred for 5 minutes and the bottom organic layer was saved and the top aqueous layer was removed. The portion which had been drained was charged back to the jacketed reactor and purified water (30 kg, 12.6 vol) was charged. The biphasic reaction mixture was stirred for 45 minutes and the bottom organic layer was removed. To the top aqueous layer was charged methylene chloride (15 kg, 4.7 vol), the biphasic reaction mixture was stirred for 5 minutes and the bottom organic layer was removed. To the top aqueous layer was charged a 50% potassium phosphate solution (29.4 kg) to reach a pH of 11.7, followed by methylene chloride (23 kg, 7.3 vol). The biphasic mixture was stirred for 5 minutes and the bottom organic layer was saved. The top aqueous layer was removed. The jacketed reactor was cleaned with purified water and acetonitrile to remove any excess aqueous layer.

The product-containing organic layers were combined and concentrated to near-dryness by rotary evaporation on one rotavap maintaining full vacuum and a bath temperature ≤50° C. The oil on the rotavap was chased with acetonitrile (5.3 kg, 1.4 vol) and the oil was dried on the rotavap for 2 hours. The oil was charged to the cleaned jacketed reactor using acetonitrile and the batch was further diluted with additional acetonitrile (67 kg total, 13.9 vol). The batch was heated to 40° C. and salicylic acid (2.9 kg, 21.0 mol, 1.33 eq) was charged under an inert atmosphere to the jacketed reactor. The batch was stirred at 45±5° C. for 1 hour, during which precipitation was observed. The batch was cooled to 1° C. over 6.5 hours and stirred at 0±5° C. for 10.5 hours. The solids were filtered onto two 18" filter funnels (5 μm nylon filter cloth used) over 1 hour. The jacketed reactor and solids were washed with cold acetonitrile (14 kg, 2.9 vol) in portions and the solids were dried on the filters under vacuum and nitrogen for 116.5 hours. A sample of the batch was removed for HPLC analysis of purity and chiral purity which showed a batch purity of 99.8% AUC and chiral purity of 100% for both filter cakes. Drying of the batch under high vacuum at 50±5° C. afforded 7880.6 g (85.9% yield) of an off-white solid.

Description 10

(S)-7-Methyl-2-(4-methyl-6-(4-(trifluoromethyl) phenyl)pyrimidin-2-yl)-1,7-diazaspiro[4.4]non-1-en-6-one (D10)

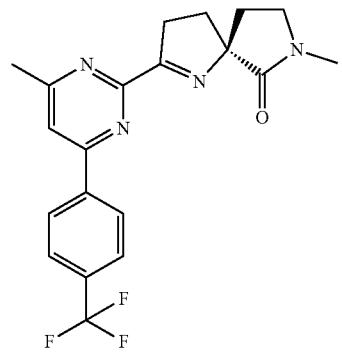

To a 100-L jacketed reactor equipped with overhead stirring, temperature probe, nitrogen inlet, and a condenser was charged (S)-3-amino-1-methyl-3-(3-(4-methyl-6-(4-(trifluoromethyl)phenyl)pyrimidin-2-yl)prop-2-yn-1-yl)pyrrolidin-2-one 2-hydroxybenzoate (5000 g, 9.5 mol, 1.00 eq; which may be prepared as described in D9) and methylene chloride (53 kg, 8.0 vol). To the resulting slurry was charged a solution of 20% potassium phosphate (7.5 kg) in water (30 kg). The biphasic mixture was stirred for 15 minutes and the pH was checked (pH observed 12.1). The mixture was stirred for an additional hour and the layers were allowed to separate, after which the bottom product-containing layer was removed. The aqueous layer was back-extracted with methylene chloride (20 kg, 3.0 vol) and the organic layers were combined. The combined organic layers were washed with brine (2×29 kg each) and dried over sodium sulfate (5.0 kg), which was then filtered off using an 18" filter funnel (no filter cloth used). The filter cake was washed with methylene chloride (13 kg, 1.9 vol).

The dried organic layers were charged to a cleaned jacketed reactor and a sample was removed for water content analysis by Karl Fischer which showed 0.20 wt % water present. The organic layers were concentrated by vacuum distillation to approximately 5 volumes (25 L) while maintaining a batch temperature ≤38° C. The concentrated product was chased with acetonitrile (2×20 kg, 5.0 vol each) while maintaining a batch temperature ≤40° C. To the product solution was charged additional acetonitrile (20 kg, 5.0 vol).

Using a nitrogen-inerted glove bag, silver trifluoromethanesulfonate (439 g, 1.7 mol, 0.18 eq) was charged to the jacketed reactor. The resulting solution was heated to 74° C. for 46 hours. The batch was cooled to 23° C. and drained into an HDPE drum, passing through a 0.2 μm filter capsule to remove potential solid silver residue. The reactor and filter were rinsed with acetonitrile (2.6 kg, 0.7 vol). The batch was concentrated by rotary evaporation to dryness to remove excess acetonitrile, resulting in an amber oil in the rotavap flasks. To the oil was charged methylene chloride (10.1 kg, 1.5 vol) and the resulting solution was transferred into the 100 L jacketed reactor which had been cleaned to remove silver residue. The rotavap flasks were rinsed with methylene chloride (10.1 kg, 1.5 vol) which was transferred to the jacketed reactor. Additional methylene chloride (44 kg, 6.6 vol) was charged to the jacketed reactor to dilute the batch.

The batch was washed with 20% sodium carbonate solution (25 kg), followed by 10% sodium thiosulfate solution (3×33 kg), and lastly with brine (30 kg) in order to remove silver from the batch. For each wash, the biphasic mixture was stirred for 15-45 minutes, the layers separated, and the aqueous layer removed. The batch was dried over sodium sulfate (3.7 kg), which was then filtered off using an 18" filter funnel (no filter cloth used). The filter cake was washed with methylene chloride (10 kg, 1.5 vol).

The dried organic layers were concentrated to dryness by rotary evaporation over 9.5 hours. The batch was further dried on the rotavap under high vacuum with a bath temperature ≤50° C. for 8 hours to remove excess acetonitrile and methylene chloride, resulting in a hard solid caked to the rotavap flask 3578.1 g (97.0% yield) of a yellow solid.

Example 1

(2R,5S)-7-Methyl-2-(4-methyl-6-(4-(trifluoromethyl)phenyl)pyrimidin-2-yl)-1,7-diazaspiro[4.4]nonan-6-one sulfate (E1)

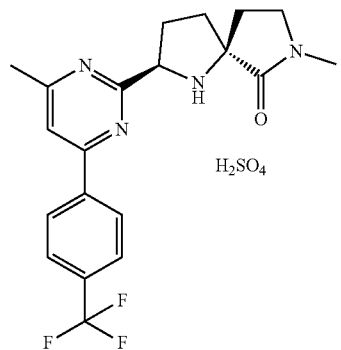

To the rotavap flask containing (S)-7-methyl-2-(4-methyl-6-(4-(trifluoromethyl)phenyl)pyrimidin-2-yl)-1,7-diazaspiro[4.4]non-1-en-6-one (3526 g, 9.1 mol, 1.00 eq; which may be prepared as described in D10) was charged methylene chloride (6.0 kg, 1.3 vol). The resulting mixture was stirred on the rotavap until complete dissolution occurred (the rotavap bath was heated to 30° C.). To a 100-L jacketed reactor equipped with overhead stirring, temperature probe, nitrogen inlet, and a condenser was charged half of the solution and the reactor was diluted further with methylene chloride (16.8 kg, 7.2 vol). The resulting solution was cooled to −23° C. and held overnight.

To a 12-L round-bottom flask equipped with overhead stirring and nitrogen inlet was charged borane tert-butylamine complex (431 g, 4.8 mol, 1.07 eq) and methylene chloride (5.8 kg, 2.5 vol). The contents of the round-bottom flask were mixed until an opaque solution was formed. The solution was charged by piston pump from the 12-L round-bottom flask to the 100-L jacketed reactor over 40 minutes while maintaining a batch temperature ≤−13° C. Methylene chloride (0.9 kg, 0.4 vol) was used to rinse the round-bottom flask, which was then transferred through the piston pump to the 100-L jacketed reactor.

The contents of the 100-L jacketed reactor were stirred while maintaining a batch temperature ≤−13° C. for 95 minutes, after which a sample was taken for reaction completion analysis by HPLC), which showed 0.18% imine remaining (relative to product) with a diastereoselectivity of 7.9:1. The batch was heated to 4° C. over 1 hour.

To the heated reaction solution was charged 5M hydrochloric acid (9.8 kg) over 58 minutes while maintaining a batch temperature ≤8° C. The batch was heated to 20° C. and stirred at 20±5° C. for 35 minutes. The pH of the batch was adjusted to 11.8 using 50% potassium phosphate solution (29.5 kg). The resulting biphasic mixture was stirred for 15 minutes and the organic product-containing layer was removed and set aside. The aqueous layer was back extracted with methylene chloride (14 kg, 5.9 vol) and the organic layers were combined. The combined organic layers were washed with brine (19.9 kg) and the resulting organic layer was retained.

To the 100-L jacketed reactor which was cleaned with purified water, acetone, and methylene chloride was charged the remainder of the (S)-7-methyl-2-(4-methyl-6-(4-(trifluoromethyl)phenyl)pyrimidin-2-yl)-1,7-diazaspiro [4.4]non-1-en-6-one and the reactor was diluted with methylene chloride (17.3 kg, 7.4 vol). The resulting solution was cooled to −13° C.

And reacted with borane tert-butylamine complex (426 g, 4.8 mol, 1.05 eq) and worked up in a similar fashion top the first portion above. After washing with brine, the two product solutions were combined in the 100-L jacketed reactor and the batch was dried over sodium sulfate (3.6 kg), which was then filtered off using an 18" filter funnel (no filter cloth used). The filter cake was washed with methylene chloride (12.3 kg, 2.6 vol).

The clean 100-L jacketed reactor was charged with the organic filtrates, and the container holding the filtrates was rinsed with methylene chloride (1.4 kg, 0.3 vol). The filtrate was concentrated by vacuum distillation to approximately 3 volumes (11 L). The concentrated product was chased with acetonitrile (2×10 kg, 3.5 vol each). To the product solution was charged additional acetonitrile (30.2 kg, 11.0 vol) and the batch was cooled to 25° C. and the reactor was reconfigured for reflux.

The contents of the jacketed reactor was heated to 46° C. and a solution of 7.5M sulfuric acid (1.7 kg 1.06 eq) was charged using a piston pump over 20 minutes. The batch was stirred for 30 minutes, during which precipitation was observed. The batch was then cooled to 24° C. over 90 minutes and stirred for 3 hours at 20±5° C. The product was filtered off using an 18" filter funnel (5 µm nylon filter cloth used) over 30 minutes. The product was washed with 1:1 acetonitrile:tert-butyl methyl ether (2.5 kg, 1.0 vol), followed by tert-butyl methyl ether (5.2 kg, 2.0 vol). The filter cake was dried on the filter under vacuum and nitrogen for 93.5 hours, which afforded 2741 g of crude product.

To a 50-L jacketed reactor equipped with overhead stirring, temperature probe, and nitrogen inlet was charged crude product, purified water (4.5 kg, 1.6 vol), and acetone (8.3 kg, 3.0 vol). The resulting slurry was heated to 36° C. and was stirred until complete dissolution was observed. A 100-L jacketed reactor was pre-cleaned with 0.2 µm filtered purified water and 0.2 µm filtered acetone and the solution was transferred from the 50-L jacketed reactor to the 100-L jacketed reactor, passing through a 0.2 µm capsule filter.

To the solution in the 100-L jacketed reactor was charged 0.2 µm filtered acetone (42.1 kg, 15.4 vol) over 3 hours while maintaining a batch temperature of 38-40° C. During the addition, the solution self-seeded itself and precipitated with no external seeding required. The resulting slurry was stirred at 38-41° C. for 1 hour, cooled to 25° C. over 1 hour, and stirred at 20±5° C. for 18 hours. The batch was then further cooled to 5° C. over 50 minutes and stirred for 2 hours and 30 minutes at 2-5° C. The slurry was filtered using an 18" filter funnel pre-cleaned with 0.2 μm filtered acetone (5 μm Nylon filter cloth used) inside of a glove bag. The solids were washed with cooled 0.2 μm filtered acetone (2×2.15 kg, 1.6 vol total). The filter cake was allowed to dry for 16 hours and then further dried under vacuum to give product as a white solid. Yield: 2122 g, 48% from D10.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A process of preparing the compound of D6:

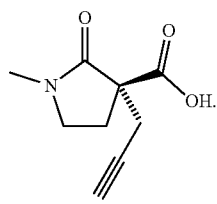

(D6)

from a compound which is (S)-1-methyl-2-oxo-3-(prop-2-yn-1-yl)pyrrolidine-3-carboxylic acid (S)-phenylglycinol salt (D5):

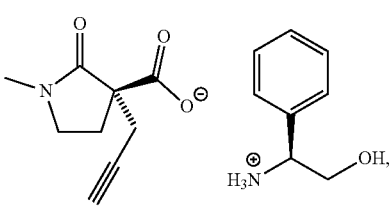

(D5)

comprising eluting a solution comprising the compound of D5 through a resin.

2. The process of claim 1, comprising preparing the compound of D5:

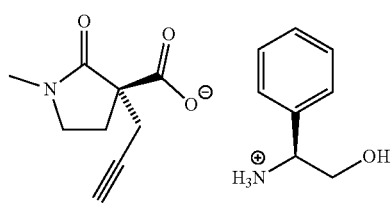

(D5)

from a compound of D4:

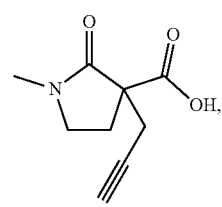

(D4)

comprising contacting the compound of D4 with S-(+)-2-phenylglycinol in a solution.

3. The process of claim 1, further comprising preparing a compound of D7:

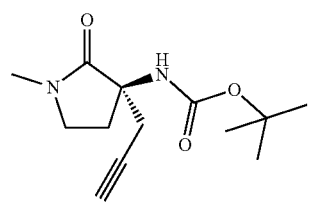

(D7)

from the compound of D6, comprising contacting the compound of D6 with a phosphoazide and a base.

4. The process of claim 3, further comprising preparing a compound of D9:

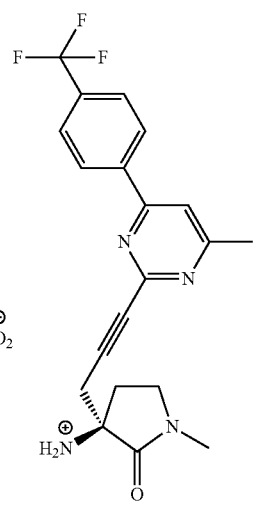

(D9)

from the compound of D7 and a compound of D8:

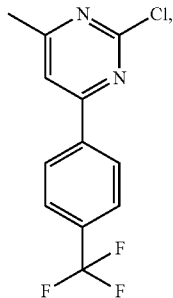
(D8)

comprising reacting the compound of D7 with the compound of D8 in the presence of a palladium catalyst, a copper salt, and a base.

5. The process of claim 4, further comprising preparing a compound of D10:

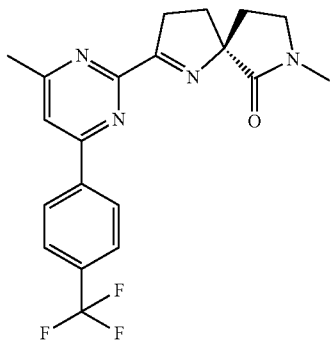
(D10)

from the compound of D9, comprising contacting the compound of D9 with a base.

6. The process of claim 5, further comprising preparing a compound of formula (I):

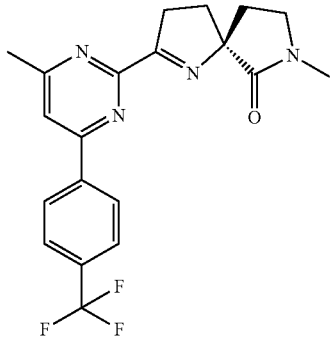
(D10)

from the compound of D10, comprising contacting the compound of D10 with a reducing agent.

7. A compound which is (S)-1-methyl-2-oxo-3-(prop-2-yn-1-yl)pyrrolidine-3-carboxylic acid (D6):

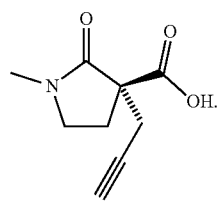
(D6)

8. The process of claim 1, wherein the solution comprises water or methanol.

9. The process of claim 1, wherein the resin is a cation-exchange resin.

10. The process of claim 9, wherein the cation-exchange resin is Dowex (50WX4) resin.

11. The process of claim 2, wherein the process further comprises a recrystallization step.

12. The process of claim 11, wherein the recrystallization step comprises seeding with crystalline (S)-1-methyl-2-oxo-3-(prop-2-yn-1-yl)pyrrolidine-3-carboxylic acid (S)-phenylglycinol salt.

13. The process of claim 3, wherein the phosphoazide is diphenylphosphorylazide.

14. The process of claim 3, wherein the base is triethylamine.

15. The process of claim 4, wherein the palladium catalyst is dichloro{bis[2-(diphenylphosphino)phenyl] ether}palladium(II).

16. The process of claim 4, wherein the copper salt is copper(I) iodide.

17. The process of claim 5, wherein the base is potassium phosphate.

18. The process of claim 6, wherein the reducing agent is a borane.

19. The process of claim 18, wherein the borane is borane tert-butylamine complex.

* * * * *